US009878115B2

(12) United States Patent
Rapoport

(10) Patent No.: US 9,878,115 B2
(45) Date of Patent: *Jan. 30, 2018

(54) SYSTEM AND METHOD FOR CIRCUITS TO ALLOW CPAP TO PROVIDE ZERO PRESSURE

(71) Applicant: New York University, New York, NY (US)

(72) Inventor: David M. Rapoport, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 20 days.

This patent is subject to a terminal disclaimer.

(21) Appl. No.: 15/005,500

(22) Filed: Jan. 25, 2016

(65) Prior Publication Data

US 2016/0136371 A1 May 19, 2016

Related U.S. Application Data

(63) Continuation of application No. 14/486,460, filed on Sep. 15, 2014, now Pat. No. 9,242,066, which is a
(Continued)

(51) Int. Cl.
*A61M 11/00* (2006.01)
*A61M 16/00* (2006.01)
(Continued)

(52) U.S. Cl.
CPC .......... *A61M 16/0069* (2014.02); *A61M 1/00* (2013.01); *A61M 16/0003* (2014.02); *A61M 16/0066* (2013.01); *A61M 16/06* (2013.01); *A61M 16/0875* (2013.01); *A61M 16/10* (2013.01); *A61M 16/20* (2013.01); *A61M 16/201* (2014.02); *A61M 16/202* (2014.02);
(Continued)

(58) Field of Classification Search
CPC ................ A61M 16/20; A61M 16/208; A61M 2202/0208; A61M 16/06; A61M 16/0066; A61M 16/204; A61M 16/209; A61M 16/205; A61M 16/202; A61M 16/0875; A61M 16/10; A61M 2016/0027; A61M 2016/003; A61M 1/00; A61M 16/0069; A61M 2202/0225; A61M 16/0003
See application file for complete search history.

(56) References Cited

U.S. PATENT DOCUMENTS

| 8,371,300 | B2 * | 2/2013 | Rapoport | .......... | A61M 16/0875 128/204.18 |
| 8,833,368 | B2 * | 9/2014 | Rapoport | .......... | A61M 16/0875 128/204.18 |
| 9,242,066 | B2 * | 1/2016 | Rapoport | .......... | A61M 16/0875 |

* cited by examiner

*Primary Examiner* — Steven Douglas
(74) *Attorney, Agent, or Firm* — Fay Kaplun & Marcin, LLP

(57) ABSTRACT

A system comprises a respiratory delivery arrangement adapted to cover at least one respiratory orifice of a patient. The system also comprises a first conduit having a first end and a second end, the second end connected to the respiratory delivery arrangement. A positive pressure is provided to the respiratory orifice via the first conduit and a second conduit having a third end and a fourth end, the fourth end connected to the respiratory delivery arrangement. An exhaled gas is extracted from the respiratory orifice by one or both of a valve configured to redirect flow through the respiratory delivery arrangement and a venturi opening.

20 Claims, 2 Drawing Sheets

Related U.S. Application Data continuation of application No. 13/759,809, filed on Feb. 5, 2013, now Pat. No. 8,833,368, which is a continuation of application No. 12/766,252, filed on Apr. 23, 2010, now Pat. No. 8,371,300.

(60) Provisional application No. 61/172,413, filed on Apr. 24, 2009.

(51) Int. Cl.
*A61M 16/08* (2006.01)
*A61M 16/10* (2006.01)
*A61M 1/00* (2006.01)
*A61M 16/06* (2006.01)
*A61M 16/20* (2006.01)

(52) U.S. Cl.
CPC ............... *A61M 2016/003* (2013.01); *A61M 2016/0027* (2013.01); *A61M 2202/0225* (2013.01); *A61M 2205/3334* (2013.01)

SYSTEM AND METHOD FOR CIRCUITS TO ALLOW CPAP TO PROVIDE ZERO PRESSURE

PRIORITY CLAIM

This application is a Continuation application of U.S. patent application Ser. No. 14/486,460 filed on Sep. 15, 2014, now U.S. Pat. No. 9,242,066, which is a Continuation application of U.S. patent application Ser. No. 13/759,809 filed on Feb. 5, 2013, now U.S. Pat. No. 8,833,368, which is a Continuation application of U.S. patent application Ser. No. 12/766,252 filed on Apr. 23, 2010, now U.S. Pat. No. 8,371,300, which claims priority to U.S. Provisional Patent Application Ser. No. 61/172,413, filed on Apr. 24, 2009. The entire disclosures of the prior patents/applications are considered as being part of the disclosure of the accompanying application and hereby expressly incorporated by reference herein.

BACKGROUND INFORMATION

Noninvasive CPAP procedures have come into widespread use for the treatment of sleep apnea and during episodes of acute and chronic respiratory failure without using endotracheal intubation. All forms of such non-invasive positive pressure ventilation (PPV) procedures require that a mask be worn over a respiratory orifice of a patient to provide an interface with a source of positive pressure. A leak port is provided on the mask to vent exhaled CO2 from the system. Current CPAP technology relies on a predetermined low pressure of greater than approximately 3-5 cm $H_2O$ to vent exhaled gas out of the leak port during exhalation. However, when a positive pressure supplied by a pressurized air source falls below this value, venting through the leak port ceases, thus causing a buildup of exhaled $CO_2$ within the mask.

SUMMARY OF THE INVENTION

The present invention is directed to systems and method for providing ventilation to a respiratory delivery system when a positive pressure being supplied by a respiratory device falls below a threshold value. In one respect, the present invention is directed to a system comprising a respiratory delivery arrangement adapted to cover at least one respiratory orifice of a patient. The system comprises a leak port located adjacent o the respiratory delivery arrangement and first conduit having a first end and a second end, the second end connected to the respiratory delivery arrangement, a positive pressure being provided to the respiratory orifice via the first conduit and a second conduit having a third end and a fourth end, the third end being separated from the first end, the fourth end connected to the respiratory delivery arrangement. The system also comprises a valve located in the first conduit and having a first position and a second position, wherein when the valve is in the first position, (a) a positive pressure flows through the first and second conduits and (b) exhaled gas from the respiratory orifice exits the leak port, and wherein, when the valve is in the second position, (c) a positive pressure flows through only the second conduit and (d) exhaled gas from the respiratory orifice exits the leak port and through the valve.

In another respect, the present invention is directed to a system comprising a respiratory delivery arrangement adapted to cover at least one respiratory orifice of a patient. The system comprises leak port located at or near the respiratory orifice. The system also comprises a first conduit having a first end, a second end, and a first valve, the first valve having a first position and second position, the second end connected to the respiratory delivery arrangement, a positive pressure being provided to the respiratory orifice via the first conduit. The system also comprises a second conduit located within the first conduit and having a third end, a fourth end and a venturi opening entraining gas from the third end to the ambient environment, the third end being separated from the first end, the fourth end connected to the respiratory delivery arrangement. When the first valve is in the first position, (a) a positive pressure flows through the first conduit and (b) a first portion of exhaled gas from the respiratory orifice exits the leak port and wherein, when the first valve is in the second position, (a) positive pressure flow through the first conduit is prevented, (b) an inhalation gas is drawn in from the opening via the first conduit, (c) a first portion of exhaled gas from the respiratory orifice exits the leak port and (d) a second portion of exhaled gas exits the venturi opening via the second conduit.

DETAILED DESCRIPTION

Figure 1:
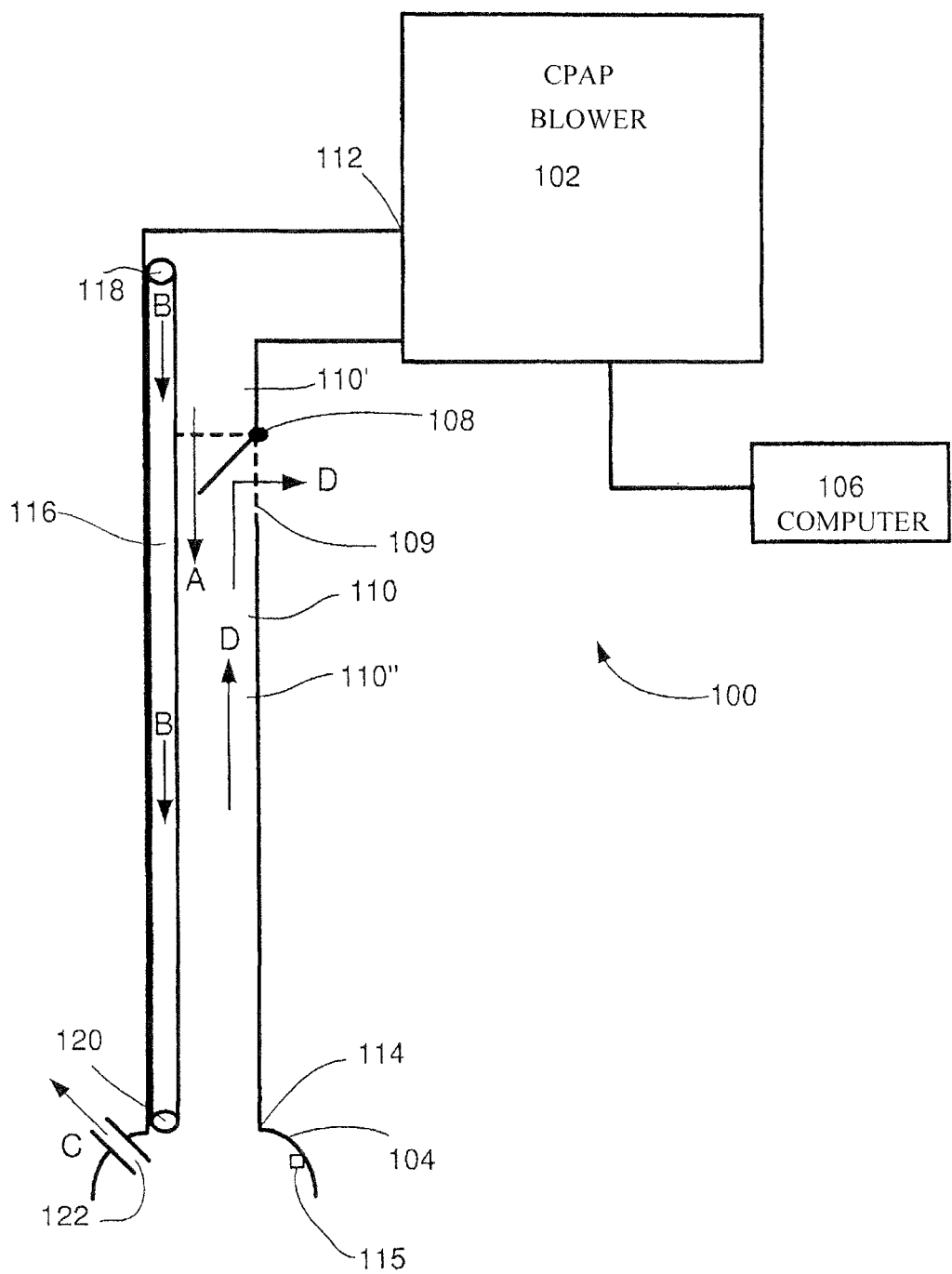
FIG. 1 shows a first exemplary embodiment of a system according to the present invention.

The present invention may be further understood with reference to the following description and the appended drawings, wherein like elements are referred to with the same reference numerals. The present invention is directed to a system and method for ventilating a CPAP system when a positive pressure being supplied by a CPAP blower falls below a predetermined threshold of approximately 3-5 cm $H_2O$ and, more specifically, when a positive pressure is at or close to zero. The exemplary embodiments of the present invention are directed to systems and methods that provide for an automatic adjustment of the CPAP device to the lowered positive pressure so that a venting of exhaled gases is permitted without any manual effort on the part of a wearer. It is noted that although embodiments of the present invention are described with respect to CPAP procedures, the present invention may be employed for the treatment of any respiratory conditions where a mask is used to administer an airway pressure including treatments for sleep apnea, hypopnea, snoring, somnolence, etc. without deviating from the spirit and scope of the present invention. As described herein, the term proximal refers to a direction approaching a CPAP device and the term distal refers to a direction approaching a respiratory mask worn over a respiratory orifice on a head of a patient.

As will be described in greater detail hereinafter, the exemplary system of the present invention is configured to prevent a buildup of exhaled gases within a CPAP system, which can be potentially harmful to a wearer of the system.

FIG. 1 shows a system 100 according to a first exemplary embodiment of the present invention. The system 100 comprises a CPAP blower 102 configured to provide pressurized air to a patient via a first conduit 110. The CPAP blower 102 is connected to a computer 106 configured to control the flow of pressurized air through the system 100, as those skilled in the art will understand. The first conduit 110 extends from a proximal end 112 connected to the CPAP blower 102 to a distal end 114 connected to a respiratory mask 104 covering a respiratory orifice (e.g., nasal cavity or oral cavity) of a patient (not shown). A leak port 122 is located on the respiratory mask 104 to provide a continuous exit of exhaled gas from the system 100 when a pressure therein is greater than approximately 3-5 cm $H_2O$. It is noted that although the leak port 122 is shown on the mask 104 of the present invention, the leak port 122 may also be positioned elsewhere on the system 100 at a location that is substantially adjacent to the respiratory orifice of the patient. The first conduit 110 is formed of a substantially flexible and durable material known in the art and is dimensioned to permit a predetermined volume of air therethrough at a predetermined pressure, as those skilled in the art will understand. The system 100 also comprises a second conduit 116 open to the mask 104. The second conduit 116 extends from a proximal end 118 open to a proximal portion of the first conduit and the CPAP blower 102 to a distal end open to the mask 104. As will be described in greater detail below, the device 100 of the present invention is configured to bypass a need for a suctioning device to draw exhaled gas out of the system. It is noted however, that an optional suctioning device may be incorporated in the system 100 without deviating from the spirit and scope of the present invention. It is further noted that although the second conduit 116 is shown to extend through the first conduit 110, the second conduit 116 may alternatively assume any position relative thereto as long as the distal end 120 opens into the mask 104 and provides a means for exhaled gas from the respiratory orifice to be removed independently of a pressure in the mask 104. For example, in a first alternate embodiment, the second conduit 116 may be located externally of the first conduit 110 as long as the proximal and distal ends 118, 120 are fluidly connected to the CPAP blower 102 and mask 104, respectively.

The system 100 also comprises a valve 108 configured to selectively seal an opening 109 located adjacent thereto. The valve 108 is a two-way valve located substantially adjacent the proximal end 112 of the first conduit 110. The valve 108 is connected to the computer 106 via one of a wired and a wireless connection. Thus, the computer 106 can automatically move the valve 108 from a first position to a second position when a predetermined condition is met, as will be described in greater detail hereinafter. In a first position, the valve 108 is configured to fluidly seal the opening 109 while leaving the first conduit 110 substantially unobstructed so that air can flow therethrough. In a second position, the valve 108 is moved so that the first conduit 110 is substantially sealed to airflow. Specifically, movement of the valve 108 to the second position fluidly seals a proximal portion 110' of the first conduit 110 located proximally of the valve 108 with respect to a distal portion 110" located distally thereof. In the second position, the opening 109 is fluidly connected to the distal portion 110" so that the distal portions 110" is open to the atmosphere, as will be described in greater detail hereinafter.

In accordance with an exemplary method of the system 100, the proximal end 112 of the first conduit 110 is connected to the CPAP blower 102 and the distal end 114 to the respiratory mask 104. When the valve 108 is in the first position (i.e., when a positive air pressure exceeding a predetermined limit is being supplied), the first and second conduits 110, 116 remain unobstructed and positive air is guided through each of the first and second conduits 110, 116 in the directions A and B, respectively. Exhaled gas from the patient is then guided out of the system 100 via the leak port 122 located on the mask 104. In an exemplary embodiment, the valve 108 remains in the first operative position as long as the positive air supply has a pressure greater than 5 cm. $H_2O$, wherein the pressure is selected based on the breathing parameters of the patient, as those skilled in the art will understand. It is noted that the system 100 may further comprise a sensor 115 located in any of the components thereof to monitor pressure and/or flow, as those skilled in the art will understand.

When the pressure of the positive air supply falls below 5 cm. $H_2O$, the valve 108 moves to the second position. Movement of the valve 108 to the second operative position ensures that exhaled $CO_2$ is properly ventilated from the system 100. Specifically, in the second position, the first conduit 110 is sealed to airflow such that positive airflow is only permitted in the direction B through the second conduit 116. The second conduit 116 is sized and shaped so that air flow therethrough has a pressure of approximately 25 l/min. Exhaled $CO_2$ from the respiratory orifice of the patient then travels in the direction C to exit the leak port 122. Furthermore, the exemplary embodiment of the present invention also guides the exhaled $CO_2$ in the direction D through the first conduit 110 and out of the opening 109. Thus, whereas present CPAP devices would prevent a leakage of $CO_2$ at low pressure, the exemplary embodiment of FIG. 1 facilitates venting of $CO_2$ from the system 100 when the air pressure in the system 100 falls below a predetermined parameter. The valve 108 remains in the second position until a CPAP air pressure once again exceeds 5 cm. $H_2O$ (e.g., when the patient returns to a sleeping state, etc.).

In another embodiment of the present invention, the valve 108 of the system 100 may shift between the first and second positions upon receipt of a signal from the sensor 115 provided in the system 100. Specifically, as those skilled in the art will understand, the sensor may be provided within one of the mask 104 or in the distal portion 110" of the first conduit 110 located distally of the valve 108, the sensor 115 being configured to measure the patient's breathing patterns and make a determination of whether the patient is in a sleep state or an awake state. As those skilled in the art will understand, the sensor 115 may be positioned anywhere within the system 100 so that the sensor 115 is provided with data corresponding to a patient's breathing patterns regardless of a position of the valve 108. The sensor 115 may be connected to a database containing data corresponding to breathing patterns indicative of each of the two states. The database may be compiled with data from the patient or from a plurality of test subjects, as those skilled in the art will understand. The valve 108 may then be configured to remain in the first position when the patient is in the sleep state. As described in greater detail earlier, in the first position, the opening 109 may be sealed so that a positive air flows travels in the directions A, B and the leak port 122 permits exhaled gas to leave the system 100. When the sensor 115 indicates that the patient has awakened, the valve 108 may move to the second position so that the opening 109 is open to the environment. Movement of the valve 108 from the first position to the second position then prevents air flow from the CPAP blower to travel through the first conduit 110 to the patient, as described in greater detail earlier.

Figure 2:
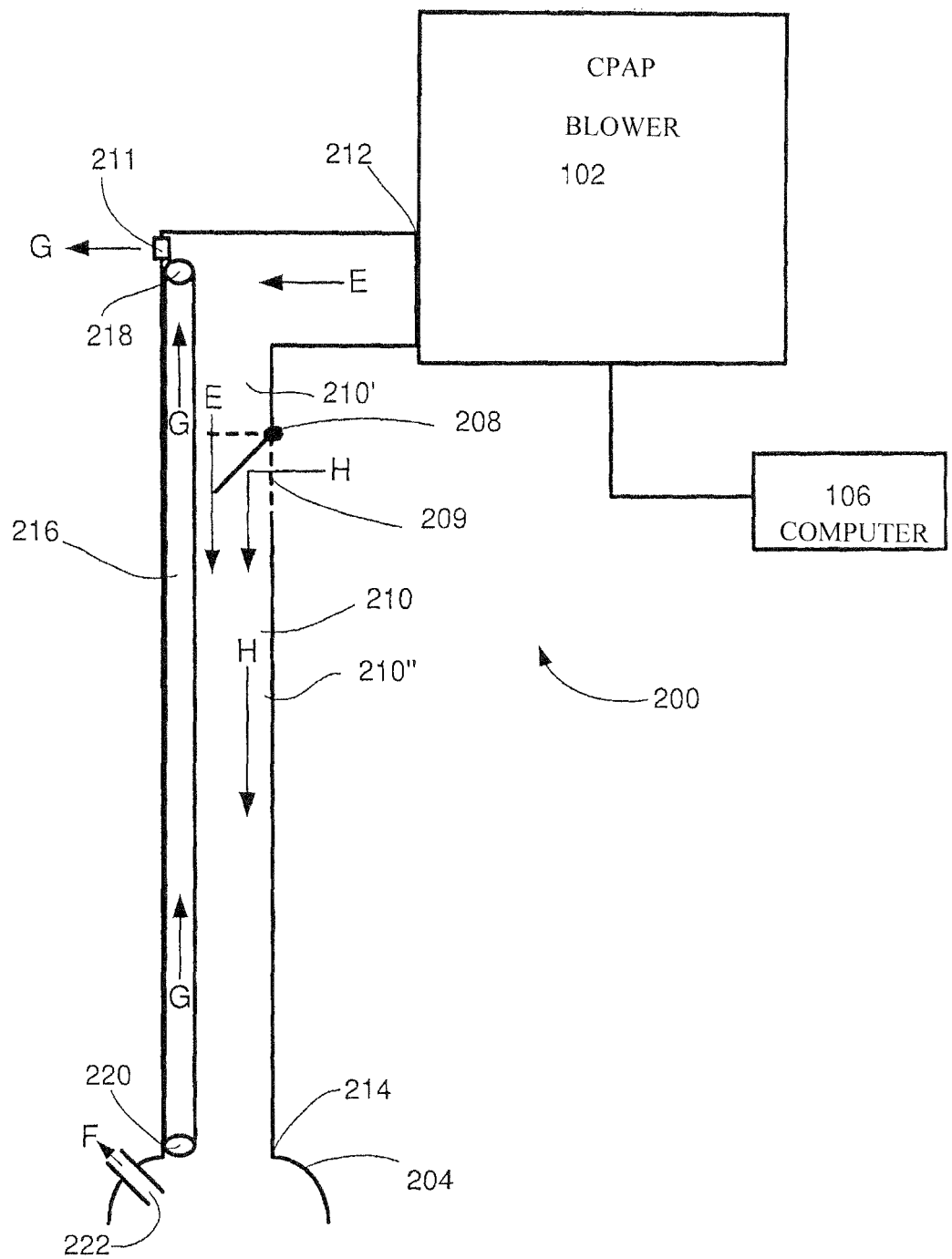
FIG. 2 shows a second exemplary embodiment of a system according to the present invention.

FIG. 2 depicts a system 200 according to an alternate embodiment of the present invention. The system 200 is formed substantially similarly as the system 100 of FIG. 1 with the exception of an additional venturi opening 211 provided therein. Specifically, the system 200 comprises a first conduit 210 extending from a proximal end 212 connected to the CPAP blower 102 to a distal end 214 connected to a respiratory mask 204 covering a respiratory orifice (e.g., nasal cavity or oral cavity) of a patient (not shown). The mask 204 comprises a leak port 222 configured to facilitate the flow of exhaled $CO_2$ out of the system 200. However, as will be described in greater detail below, the leak port 222 is optional only and may be omitted without deviating from the spirit and scope of the invention. The system 200 also comprises a second conduit 216 located within the first conduit 210. The second conduit 216 extends from a proximal end 218 to a distal end 220 open to the mask 204. The venturi opening 211 is formed as an opening on a wall of the first conduit 210 and, according to one embodiment of the present invention, is open to both the first and second conduits 210, 216. The exemplary embodiment of the present invention is configured so that when there is a low pressure within the system 200, the venturi opening 211 remains open to an ambient environment to permit entrained gas to exit therefrom. Specifically, since the proximal end 218 of the second conduit 216 is located adjacent the venturi opening 211, a flow of entrained gas through the second conduit 216 is sufficient to cause the venturi opening 211 to permit flow therethrough, as those skilled in the art will understand.

The valve 208 is a two-way valve formed substantially similarly as the valve 108. Specifically, the valve 208 is connected to the computer 106 via one of a wired and a wireless connection. In a first position, the valve 208 is configured to fluidly seal an opening 209 while leaving the first conduit 210 substantially unobstructed. In a second position, the valve 208 separates the first conduit 210 into proximal and distal portions 210', 210" and opens the opening 209 to the atmosphere, as described in greater detail earlier.

In accordance with an exemplary method for the system 200, the proximal end 212 of the first conduit 210 is connected to the CPAP blower 102 and the distal end 214 to the respiratory mask 204. When a positive air supply being supplied to the system 200 exceeds a predetermined threshold value, the valve 208 is in the first position. In this configuration, the positive air supply is directed through the first conduit 210 in the direction E. Exhaled gas from the respiratory orifice of the patient can exit the system 200 from the leak port 222 in the direction F. In one embodiment of the present invention, the venturi opening 211 may remain open when the positive air supply is being supplied. Thus, exhaled gas from the respiratory orifice may also flow proximally from the distal opening of the second conduit 216 and out of the venturi opening 211 in the direction G. It is therefore noted that, in an alternate embodiment of the invention, the leak port 222 may be omitted from the system 200 without affecting the principle of operation thereof. Specifically, the positive pressure within the system 200 may cause suction at the venturi opening 211, thus forcing a movement of gas in the direction G through the second conduit 216 and out of the venturi opening 211. However, it is submitted that this is not a required component of the present invention and that, in another exemplary embodiment, the venturi opening 211 may remain closed when positive air with a pressure above the predetermined threshold is being supplied to the system. Specifically, the system 200 may be provided with a blocking means (e.g., a valve, a plug, etc.) configured to prevent flow through the venturi opening 211 when the valve 208 is in the first position. The blocking means (not shown) may be removed from the venturi opening 211 when the valve 208 is moved to the second position, wherein a pressure of expiratory flow through the second conduit 216 may open the venturi opening 211 to permit flow thereoutof, as those skilled in the art will understand and as described in greater detail hereinafter. In an exemplary embodiment, the valve 208 remains in the first position as long as the positive air supply has a pressure greater than approximately 5 cm. $H_2O$.

When the positive air pressure falls below 5 cm. $H_2O$, the valve 208 moves to the second position. In this position, positive pressure E from the CPAP blower is prevented from entering either the first or second conduits 210, 216. Rather, the valve 208 opens the opening 209 so that atmospheric air is permitted to flow into the distal portion 210" of the first conduit 210 in the direction H. The movement of exhaled gas through the system 200 follows the same pattern as described in the first valve position wherein a first portion of exhaled gas from the respiratory orifice exits the leak port 222 in the direction F and a second portion of the exhaled gas is guided through the second conduit 216 and out of the venturi opening 211 in the direction G. Specifically, the venturi opening 211 causes a suction to be applied adjacent thereto, the suction force drawings the exhaled gas proximally from the distal end 220 of the second conduit 216 and out of the venturi opening 211. The valve 208 remains in the second operative configuration until a CPAP air pressure E once again exceeds 5 cm. $H_2O$ (e.g., when the patient returns to a sleeping state, etc.). This exemplary embodiment thus uses a valve 208 and a venturi opening 211 in combination to guide both the flow of positive and negative air through the system 200.

It is noted that various modifications may be made to the embodiments disclosed herein without deviating from the scope of the present invention. For example, although the present invention has been described with a venturi opening 211, another gas withdrawal means may be provided on the system 200. In one such exemplary embodiment, suction can be provided to the system 200 by a suction device or another suctioning means, as those skilled in the art will understand.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:
1. A system, comprising:
 a respiratory mask adapted to cover at least one respiratory orifice of a patient;
 a respiratory device configured to deliver a positive pressure gas flow;
 a first conduit extending from a first end connected to the respiratory device to a second end connected to the respiratory mask,
 a second conduit extending from a third end to a fourth end connected to the respiratory mask, the third end being separate from the first end, the fourth end connected to the respiratory mask;
 a valve located in the first conduit, the valve movable between a first position and a second position, the first position being configured to fluidly seal an opening in a wall of the first conduit, and the second position being configured to fluidly connect, via the opening, at least a portion of the first conduit to an ambient atmosphere;
 a sensing element for detecting data corresponding to a breathing pattern of a patient; and
 a controller for controlling the positive pressure gas flow based on the data detected by the sensing element, and moving the valve to the first position when the breathing pattern corresponds to the patient being in a sleep state and to the second position when the breathing pattern corresponds to the patient being in an awake state.

2. The system of claim 1, wherein the respiratory device is a CPAP blower.

3. The system of claim 1, wherein the respiratory mask comprises a leak port configured to vent a portion of exhaled gas from the at least one respiratory orifice out of the respiratory mask.

4. The system of claim 1, wherein when the valve is in the first position, the positive pressure flows through the first conduit.

5. The system of claim 4, wherein when the valve is in the first position, the positive pressure flows through the second conduit.

6. The system of claim 1, wherein when the valve is in the first position, a portion of exhaled gas from the respiratory orifice is guided out of the respiratory delivery arrangement.

7. The system of claim 1, wherein when the valve is in the second position, inhalation gas is drawn in from an ambient atmosphere via the first conduit.

8. The system of claim 1, wherein when the valve is in the second position, a portion of exhaled gas from the at least one respiratory orifice exits the system through the first conduit or the second conduit.

9. The system of claim 1, further comprising a suction withdrawal arrangement operably associated with the respiratory mask to aid in withdrawal of exhaled gases thereoutof.

10. A method, comprising:
positioning a respiratory mask to cover at least one respiratory orifice of a patient, the respiratory mask being connected to a first conduit and a second conduit, the first conduit extends from a first end connected to a respiratory device configured to deliver a positive pressure gas flow to a second end connected to the respiratory mask, the first conduit including a valve movable between a first position and a second position, and the second conduit extends from a third end to a fourth end connected to the respiratory mask, the third end being separate from the first end;
monitoring data corresponding to a breathing pattern of the patient;
delivering the positive pressure gas flow at a predetermined pressure from the respiratory device to the first conduit, the predetermined pressure being adjusted based on the data; and
controlling the valve so that when the breathing pattern corresponds to the patient being in a sleep state, the valve is moved to the first position to fluidly seal an opening in a wall of the first conduit, and when the breathing pattern corresponds to the patient being in an awake state, the valve is moved to the second position to fluidly connect, via the opening, at least a portion of the first conduit to an ambient atmosphere.

11. The method of claim 10, wherein the patient suffers from sleep apnea.

12. The method of claim 10, wherein the respiratory device is a CPAP blower.

13. The method of claim 10, wherein when the valve is in the first position, the positive pressure flows through the first conduit.

14. The method of claim 13, wherein when the valve is in the first position, the positive pressure flows through the second conduit.

15. The method of claim 10, wherein when the valve is in the first position, a portion of exhaled gas from the respiratory orifice is guided out of the respiratory delivery arrangement.

16. The method of claim 10, wherein when the valve is in the second position, inhalation gas is drawn in from an ambient atmosphere via the first conduit.

17. The method of claim 10, wherein when the valve is in the second position, a portion of exhaled gas from the at least one respiratory orifice exits the system through the first conduit or the second conduit.

18. The method of claim 10, further comprising the step of applying suction to the respiratory mask via a further opening formed through one of the first and second conduits.

19. The method of claim 18, wherein suction is applied by a suction device.

20. The method of claim 18, wherein the suction is applied by a venturi opening formed through the second conduit.

* * * * *